United States Patent [19]

Edamatsu et al.

[11] 4,446,481

[45] * May 1, 1984

[54] AUTOMATIC PRODUCT INSPECTION SYSTEM

[75] Inventors: Kunihiko Edamatsu; Takayoshi Makabe, both of Kanagawa, Japan

[73] Assignee: Fuji Electric Co., Ltd., Kawasaki, Japan

[*] Notice: The portion of the term of this patent subsequent to Jan. 1, 2000 has been disclaimed.

[21] Appl. No.: 137,548

[22] Filed: Apr. 4, 1980

[30] Foreign Application Priority Data

Apr. 5, 1979 [JP] Japan ................................. 54-41332

[51] Int. Cl.³ .............................................. H04M 7/18
[52] U.S. Cl. .................................... 358/106; 356/237; 250/563
[58] Field of Search ................ 358/101, 106; 356/237, 356/239; 250/562, 563; 382/8

[56] References Cited

U.S. PATENT DOCUMENTS

| | | | |
|---|---|---|---|
| 3,887,762 | 6/1975 | Umo et al. | 358/106 |
| 4,185,298 | 1/1980 | Billet et al. | 358/106 |
| 4,207,593 | 6/1980 | Deutsch | 358/106 |
| 4,277,803 | 7/1981 | Sano | 358/106 |

Primary Examiner—Tommy P. Chin
Assistant Examiner—Edward L. Coles
Attorney, Agent, or Firm—Bruce L. Birchard

[57] ABSTRACT

An automatic system for inspecting products having an edge or edges which, for an acceptable product, are straight (within predetermined tolerances) without accurate orientation of such products which includes a raster-scanned television camera (or its equivalent) for generating a composite video signal corresponding to the product being inspected. The number of horizontal sweep intervals in each edge to determine its length and comparing such length information with pre-stored reference length to determine if the two correspond, rejecting the capsule if it is shorter than the reference length but, if it is longer than the acceptable length, determining if the greater length is a result of the product's being tilted or torn.

6 Claims, 10 Drawing Figures

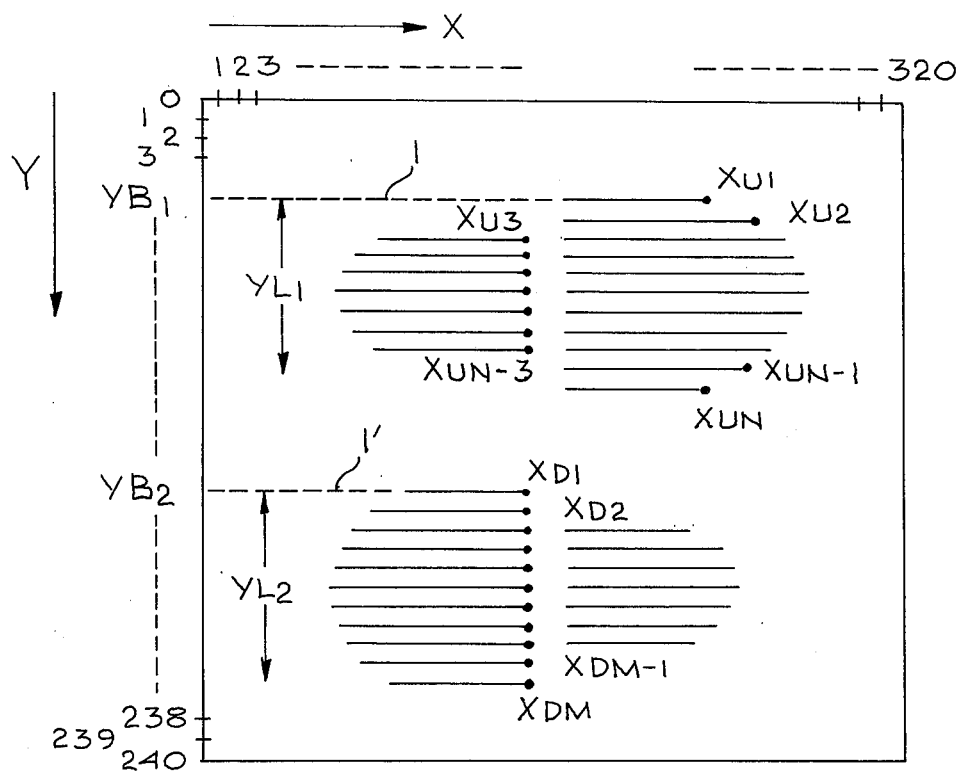
FIG. 5
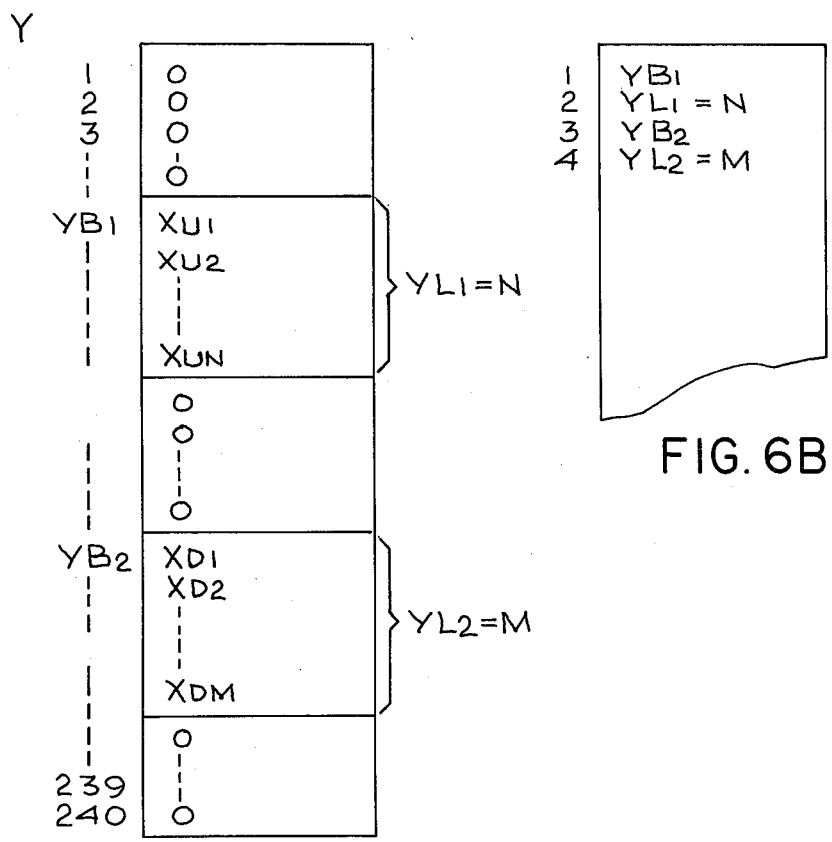
FIG. 6A
FIG. 6B

AUTOMATIC PRODUCT INSPECTION SYSTEM

BACKGROUND OF THE INVENTION

1. Field of the Invention

This invention relates to automatic product inspection systems and methods.

2. Prior Art

Automatic inspection of products has been done, in the past, by means of pattern comparisons. Such systems involve the use of masks, or the like, and require accurate orientation of the product being inspected. Such orientation is time consuming and difficult. Visual inspection, which has been used in the past for drug capsule and semi-conductor chip products, is slow, monotonous and inaccurate. Operators soon become tired and errors rise intolerably.

Therefore, it is an object of this invention to provide a novel product inspection system which is free of the problems experienced in connection with the use of prior art systems.

It is a further object of this invention to provide an automatic inspection system for products which, when acceptable, have straight edges of predetermined length, such system requiring no accurate orientation of the products.

SUMMARY OF THE INVENTION

Stated succinctly, a scanning, photo-electric transducer, for example a television camera, views the products, for example drug capsules, being carried on a conveyor belt with minimally controlled orientation. The video signal derived as the products are moved into the view of the raster-scanned television camera (and are simultaneously illuminated, as by a strobe lamp) is stripped of its synch pulses and is shaped into a binary signal. Transitions from "zero" to "one" and from "one" to "zero" are detected along each horizontal scanning line. Those transitions indicate a change in the image seen by the camera. More specifically, a point along any edge will thus be indicated.

The length of any edge is determined by counting the number of horizontal sweep intervals it contains. If that length is shorter than a stored reference length, a reject signal is generated. If the length is acceptable further analysis is done to determine if the incorrect length is a result of the product's being tilted, or the edges thereof curved or torn. That analysis includes subtracting the "X" minimum coordinate from the "X" maximum coordinate along the maximum line length measured in the "Y" direction and comparing the result with a reference value. If X max-X min does not exceed a predetermined value the product is passed, while if X max-X min exceeds that value further analysis occurs.

A summation of incremental "Y" lengths for a series of incremental "X" changes in a uniform direction is compared with a third reference value and if it is smaller than this value, a curved line is indicated and a reject signal is generated, while; if it is not smaller than this reference value another analysis takes place.

Finally, the difference between the mean or average value of the "Y" increments in a region and each value of such "Y" increments is compared with a reference value and if it exceeds that value a reject signal is generated while, if the reference value is satisfied the product (in this case a drug capsule) is passed.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description taken in conjunction with the accompanying drawings, in which:

FIG. 5 is a diagrammatic representation of the scanning pattern utilized in the present system showing binary transition points;

FIG. 6 is a memory map of certain coordinate and length values determined for a particular product by the system of FIG. 3;

DETAILED DESCRIPTION OF THE PREFERRED EMBODIMENTS

Figure 1A:
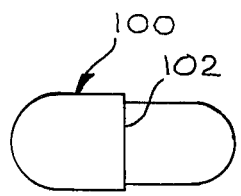
FIG. 1 is an outline drawing showing the profile of two products having straight edges which could be inspected by the system of the present invention.
Figure 1B:
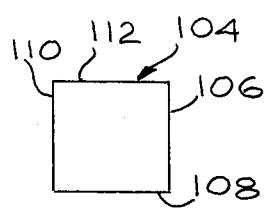

In FIG. 1 A, capsule 100 is shown having an edge 102 which, for an acceptable capsule, is straight, as shown. The product of FIG. 1 B may be a semiconductor substrate or chip 104 which has multiple edges 106, 108, 110, 112, which, for an acceptable product should be straight. These are the types of edges which, it is intended, be automatically checked by this system and method. Cardboard boxes are included. The projections of the edges on the X and Y axes are straight lines.

Figure 2A:
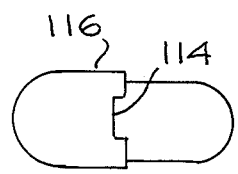
FIG. 2 is an outline drawing showing the type of defect which can be detected with the system of the present invention.
Figure 2B:
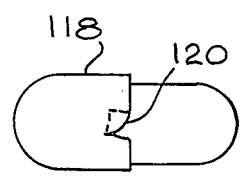

In FIG. 2 A a section 114 has been lost from cap 116. In FIG. 2 B the cap 118 has been torn and folded under at 120. Both of these defects can be detected by this system and method at high speed and with great accuracy.

Figure 3:
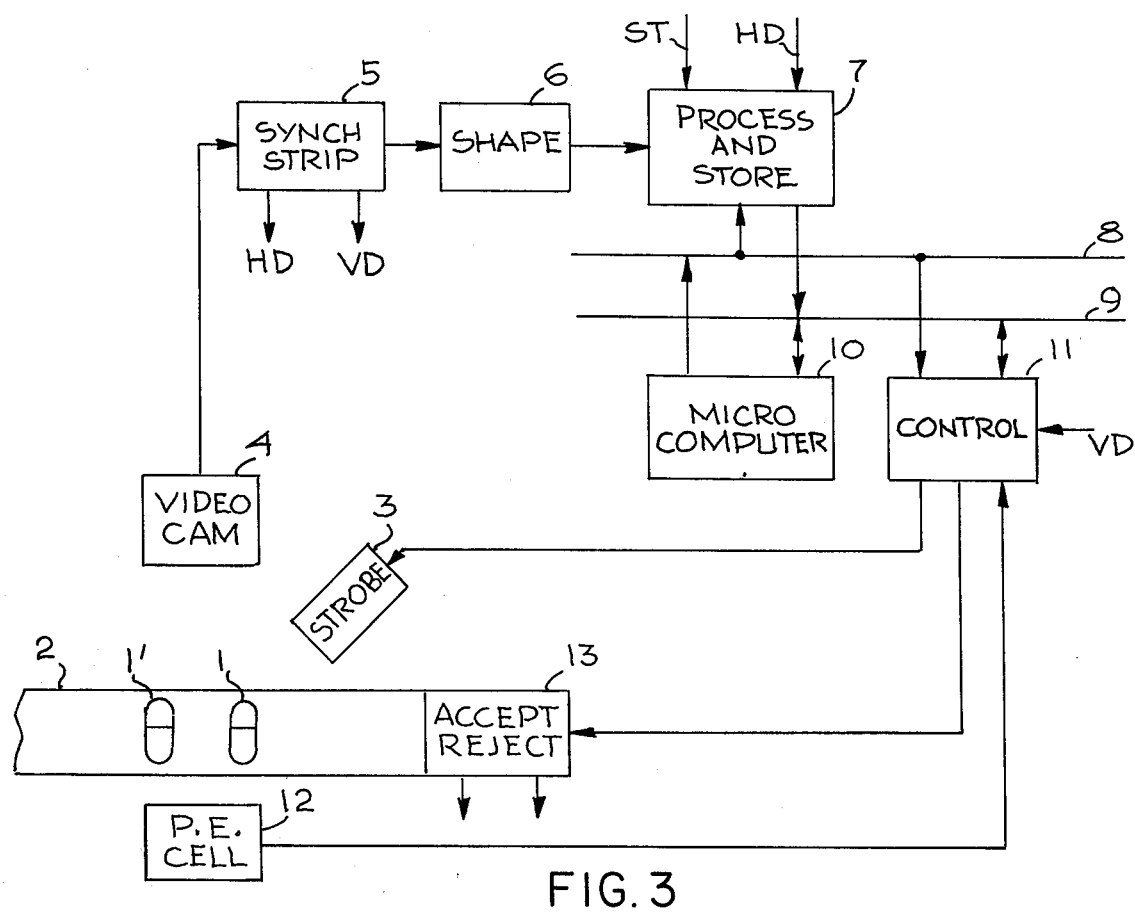
FIG. 3 is a block diagram of the inspection system according to the present invention.
Figure 4A:
FIG. 4 is a diagram showing the timing relationship between certain pulses in the system of FIG. 3.
Figure 4B:
Figure 4C:
Figure 4D:
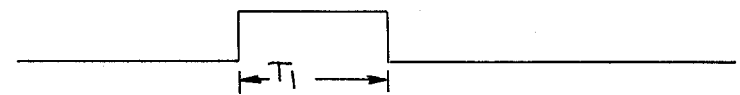
Figure 4E:
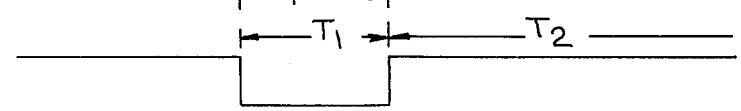

FIG. 3 shows a block diagram of the inspection system according to this invention. In FIG. 3 capsules 1 and 1' are carried in recesses on conveyor belt 2. The recesses only nominally orient the capsules. Accurate orientation, as would be required in a pattern recognition system, is not required with this system.

Capsules 1 and 1' are illuminated by strobe light 3 as they pass within the field of view of image converter 4, which may be an industrial television camera with conventional raster scan.

The composite television signal from camera 4 passes to synch stripper 5, where the horizontal synch pulses HD and the vertical synch pulses, VD, are removed, leaving the video signal envelope, which is applied to signal shaper 6, from which a squared, or binary signal emerges for application to signal processing and storage circuit 7. The functions performed in circuit 7 are set forth in more detail in FIG. 7. A microcomputer 10 addresses the memory in circuit 7 through address bus 8 and extracts data for processing from data bus 9. Control circuit 11 receives processed data signals from microcomputer 10 and supplies control signals to it. Control circuit 11 also receives vertical drive (VD) information from synch stripper 5, and capsule position information from photo-electric cell 3. It supplies a strobe trigger (ST) pulse to strobe 3 and an accept-reject signal to ejection control circuit 13.

In FIG. 4, curve A shows the pulse applied to control circuit 11 from position sensor 12 when a capsule 1 is within the field of view of camera 4. This pulse of FIG. 4, curve A enables control circuit 11, which also receives the vertical synch or drive pulses VD shown in FIG. 4B to supply a trigger pulse (ST), shown in FIG. 4 C, to strobe 3 in synchronism with the beginning of a vertical sweep interval, $T_1$, FIG. 4 D, during which period microcomputer 10 is put in a "hold" condition as shown in FIG. 4 E. During the period $T_2$(FIG. 4 E) the Microcomputer 10 performs its analysis of stored data in circuit 7.

In FIG. 5, the video pattern of capsules 1 and 1' is shown in binary form, i.e. after shaping in shaping circuit 6, and on a horizontal-line-by-horizontal basis. As can be seen, capsule 1 starts at the "Y" coordinate $YB_1$ and has a diameter measured in horizontal lines of $X_{UN}$ which is shown as $YL_1$.

The profile of capsule 1' has its first video segment at the "Y" coordinate $YB_2$ and its width (the diameter of capsule 1') in terms of horizontal lines is $X_{DM}$ which is shown as $YL_2$ in FIG. 5. The transition points in the shaped video are aligned, showing an un-mutilated and acceptable capsule edge at the joint between the two halves of each capsule.

As can be seen from FIG. 5 the vertical resolution of this system is 240 lines and the horizontal resolution is 320 lines.

In FIG. 6 the information inherent in FIG. 5 is presented in memory map or chart form with "Y" coordinates as addresses. Until "Y" coordinate $YB_1$ is reached the data stored at each address is a "zero" in binary terms. After it reaches $YB_1$ the shaped video signal goes to a "one" because the upper edge of the outer cap of capsule 1 is detected by camera 4 and then the data stored are $X_{U1}$ thru $X_{UN}$ at respective addresses. The extent of horizontal lines $X_{U1}$ through $X_{UN}$ is the transverse or width dimension of capsule 1 in terms of horizontal lines, the separation of which is determined by the vertical deflection circuits of camera 4.

The binary signal falls to zero again when the camera is scanning the space between capsules 1 and 1' and, at $YB_2$ the top edge of capsule 1' produces video output and a "one" in binary terms, which continues for M horizontal lines from $X_{D1}$ to $X_{DM}$ to give a diameter length of $YL_2$. The video and binary signals then return to zero. This information is stored in Y coordinate memory.

FIG. 6 B shows the storage of edge length data (as projected on the "Y" axis) for capsules 1 and 1'.

Figure 7:
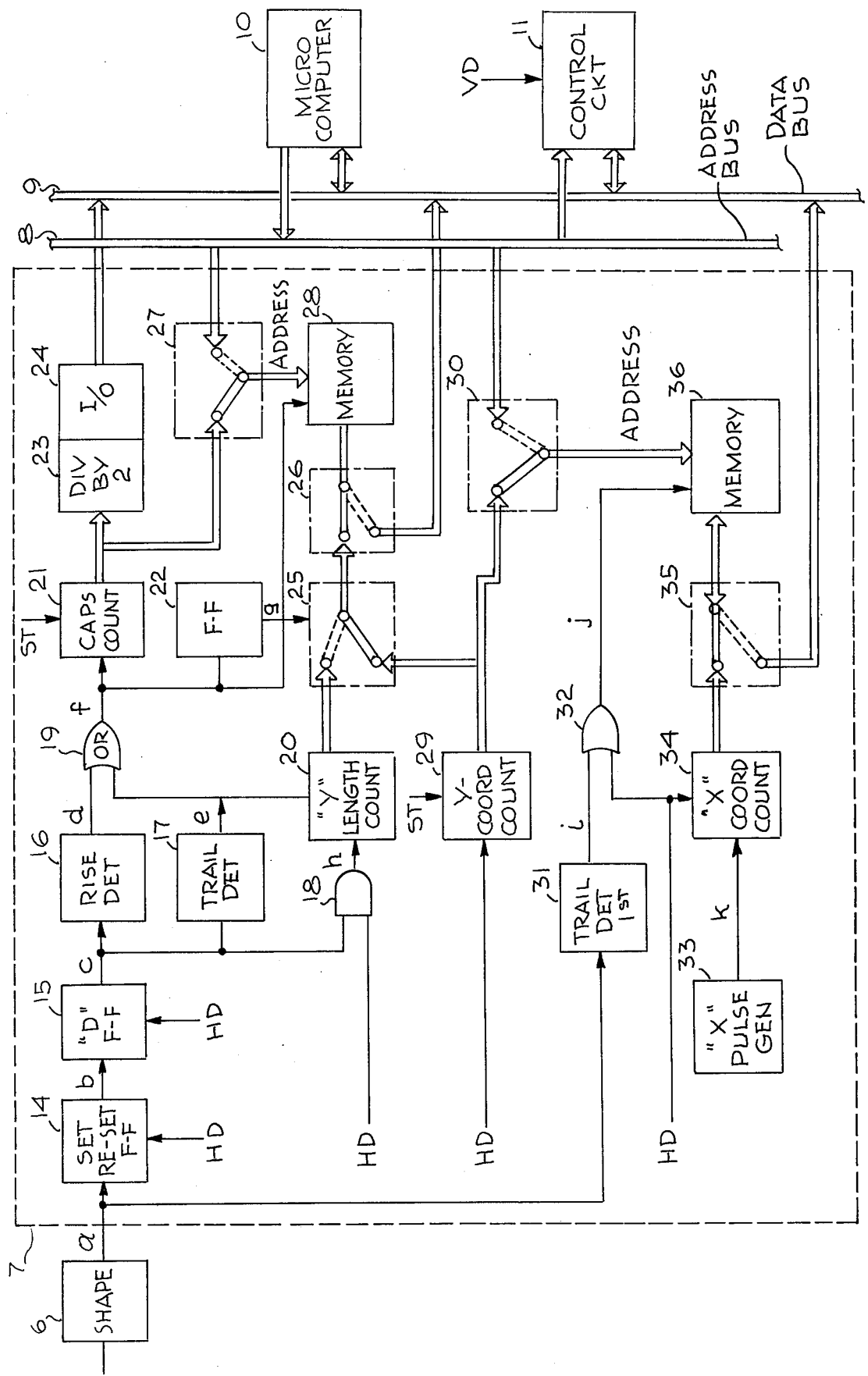
FIG. 7 is a block diagram of a portion of the system of FIG. 3.

In FIG. 7, signal processing and storage circuit 7 includes a set, re-set flip-flop 14 which may be a type SN74LS107 with an SN7400 and an SN7404. This flip-flop is set by the leading edge of the shaped video signal "a" shown in line (E) of FIG. 8. Flip-flop 14 also receives horizontal drive pulses HD and is re-set by the trailing edge of the next horizontal drive pulse, as shown in lines "F" and "G" of FIG. 8. That pulse train is fed to "D"-type flip-flop 15, which additionally receives horizontal synch or drive pulses HD. The leading edge of horizontal drive pulse which reset flip-flop 14 turns on flip-flop 15 and that flip-flop remains on, or in a "one" state, until the arrival of the trailing edge of the first horizontal drive pulse which arrives when curve "b" of FIG. 1 is a "zero". The resulting gating signal is shown at line (H) signal "c" of FIG. 8.

The signal "c" is fed to leading edge or rising detector 16, which may be an SN74LS107 with an SN7400. The result is the generation of signal "d", line (I), FIG. 8.

Signal "c" is also fed to trailing edge detector 17 which may be an SN74LS107 with an SN7400. The resulting signal "e" is shown at line "J" of FIG. 8.

Figure 8:
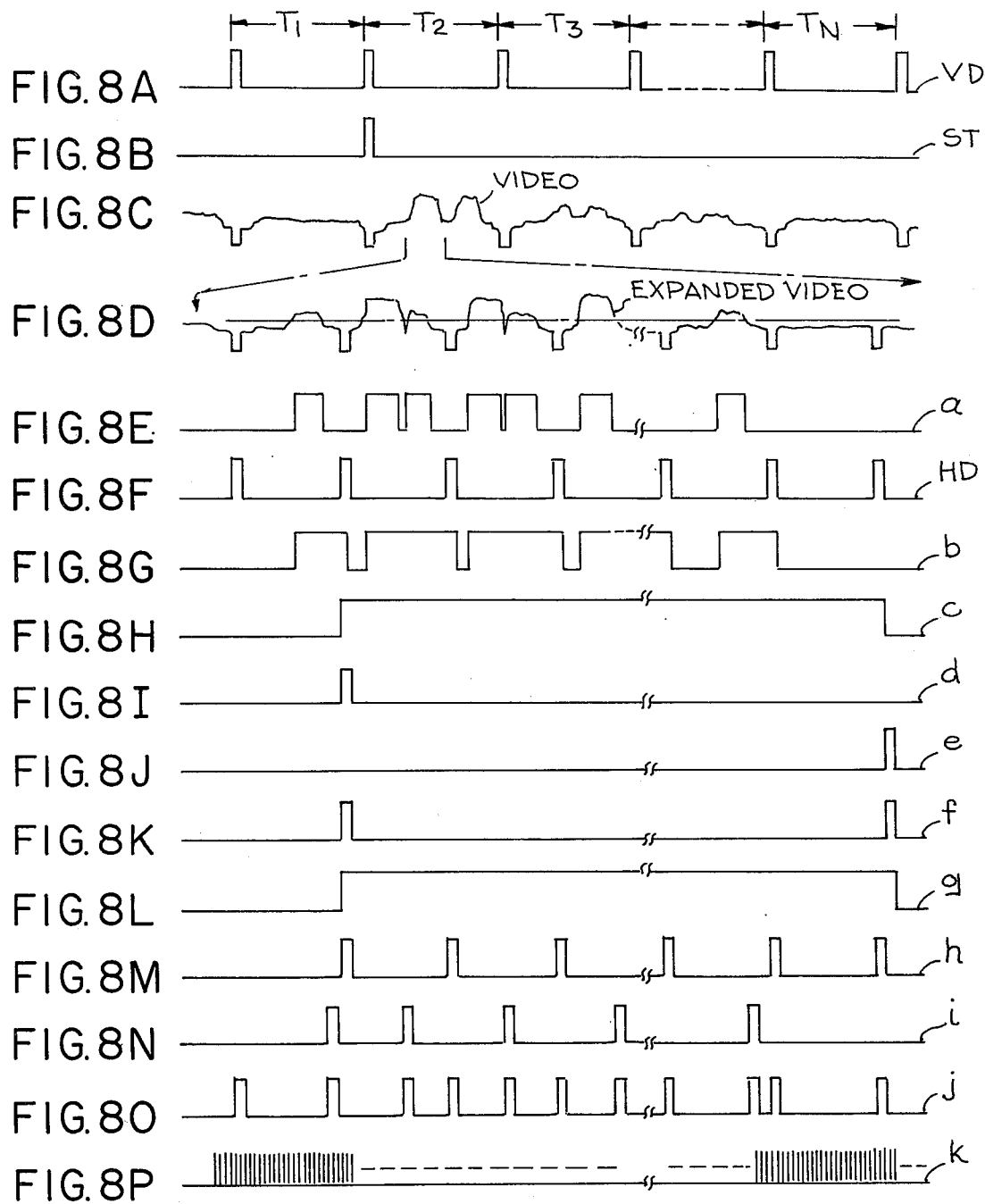
FIG. 8 is a timing diagram for the system portion of FIG. 6.

Signals "d" and "e" are fed to "OR" gate 19 (which may be an SN7400) and the resulting signal is shown as signal "f" at line "K" of FIG. 8.

Signal "f" controls flip-flop 22 to produce switching signal "g" shown at line "L" of FIG. 8. Signal "g" switches switch 25 to the solid-line position shown when signal "g" is a "one", and "Y" coordinate data is stored in memory 28. When signal "g" is a "zero" switch 25 goes to the dotted-line position and "Y" length data goes into memory 28.

Signal "c" also is fed to "and" gate 18 which is receiving horizontal drive pulses HD. "And" gate 18 may be a type SN74161N. The resulting signal is shown as "h" in FIG. 8 and is the number of horizontal intervals within gate "g". That signal "h" is fed to "Y"-length counter 20 which may be an SN74161N. Thus the length of an edge is determined in terms of number of horizontal lines it spans.

Signal "f", in addition to being fed to flip-flop 22 is fed to capsule-number counter 21, which may be an SN74161N. Counter 21 receives a strobe trigger signal (ST) which coincides with a vertical synch pulse, and puts out a capsule count signal as an address signal to memory 28.

The signal from capsule counter 21 is fed to the divide-by-two circuit 23, which may be an SN74161N, and through I/O device 24, which may be an SN74367N, to data bus 9.

Signal "a", in addition to being fed to set-reset flip-flop 14 is fed to trailing edge detector 31 which is effective to detect the first trailing edge in each horizontal interval of signal "a". The signal "i" appearing at line "N" of FIG. 8 is thus produced and fed to "OR" gate 32, to which horizontal drive pulses HD are also fed. The "OR" gate 32 may be an SN7400. The output of "OR" gate 32 is a signal "j" shown at line (0) in FIG. 8.

This signal "j" is fed to memory 36 to which is also fed the pulses, at the rate of 320 per horizontal line, out of "X" coordinate counter 34 which also receives horizontal drive pulses. Counter 34 determines the "X" coordinate of any "Y" increment, as will be discussed in connection with FIG. 10 E.

After signal "g" returns to "zero" the control circuit 11 switches changeover circuits 25, 26, 27, 30 and 35 from the "write" to the "read" mode and microcomputer 10 processes the stored data to determine if any detected edge is straight, free of defects and of the right length. If these criteria are met the capsule is accepted, if not it is rejected by accept-reject mechanism 13.

Changeover circuits 25, 27 and 30 may be of type SN74157N. Changeover circuit 26 may be an SN74368N. Changeover circuit 35 may be an Intel 8216. Memory 36 may be a 2112A-4 of Intel.

Figure 9:
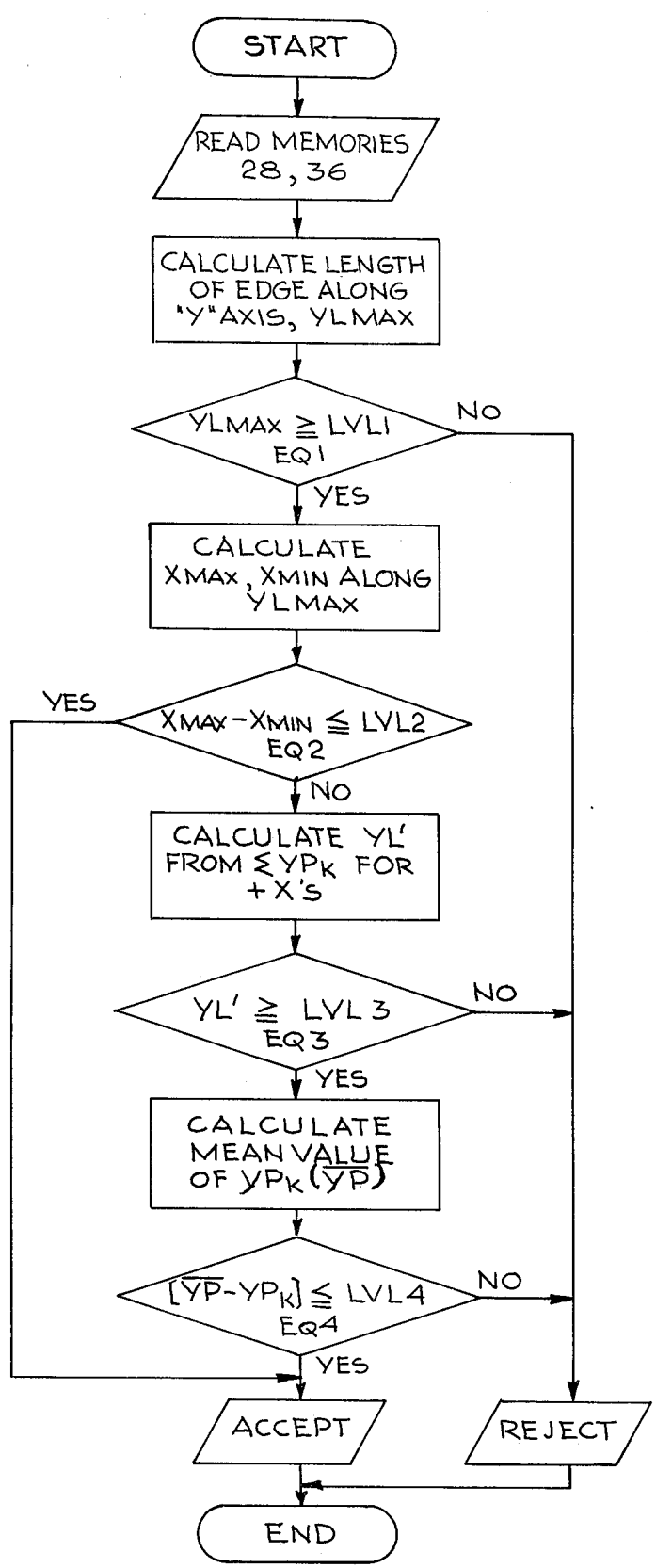
FIG. 9 is a flow chart of the microcomputer operations in the system of FIG. 3.
Figure 10A:
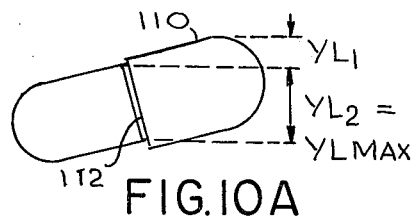
FIG. 10 A through E is a series of diagrams showing various coordinate and length data used in the inspection analysis process performed by the microcomputer.
Figure 10B:
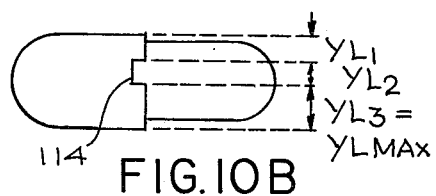
Figure 10C:
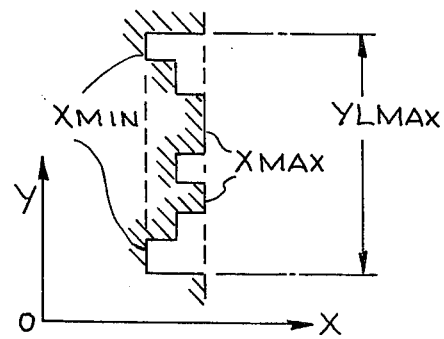
Figure 10D:
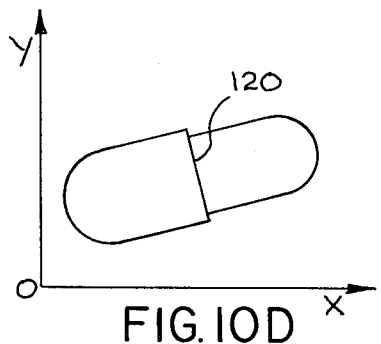
Figure 10E:
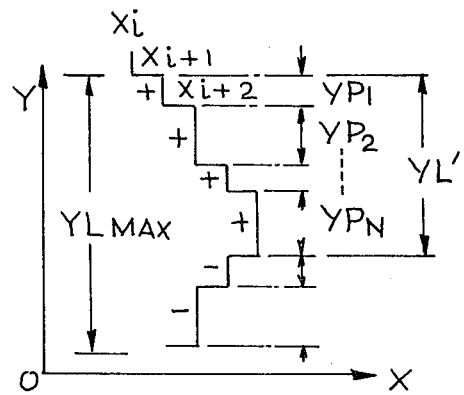

FIG. 9 shows the calculation functions performed by microcomputer 10 when signal "g" goes to zero and outside the "hold" time $T_1$ in FIG. 4.

FIG. 9 can best be discussed in connection with FIG. 10.

At the outset, X-coordinates representing an edge of the examined object are read out from memory 36 and a transverse dimension YL is found over which the difference between the X-coordinates of the edge being studied for successive horizontal lines does not exceed 1. (Here, coordinates are given by integers). In FIG. 10 A, two edges are seen by the camera 4. One is edge 110 and the other is edge 112. As projected on the "Y" axis edge 110 has a length $YL_1$ and edge 112 has a length $YL_2$. Computer 10 will judge edge 112 as having the maximum length YL max and will compare that length with a reference length LVL1. If YL max is smaller than LVL1 a reject signal will be sent to accept-reject control 13, FIG. 3.

If YL max≧(LVL1 (Eq. 1), the analysis will continue by subtracting X min (along YL max) from X max (along YL max). If the result satisfies the equation: X max−X min≦LVL2 (Eq. 2), it indicates that the edge under consideration is relatively straight and untorn. For example, if the capsule is properly oriented and the edge is straight X max-X min will equal zero and the second test is met. If the outer cap has a notch in it, as at 120 in FIG. 2 B, while the first test of length might be satisfied, the second test of X max-X min over the length YL max would not be satisfied. X max and X min are seen in FIG. 10 C. If the second equation is not satisfied, the analysis continues to determine if the reason is tilting of the capsule, as shown in FIG. 10 D. Edge 120, which is of interest, would satisfy the first test, not the second test.

As can be seen from FIG. 10 E, values of the length of Y for successively evenly increased values of $X(YP_1 \Rightarrow YP_N)$ can be summated, to form the values VL', and compared with a third reference value LVL3. If equation 3:

YL'≧LVL3 (Eq. 3), is not satisfied, a reject signal is sent to accept-reject unit 13 (FIG. 3). If equation 3 is satisfied, a further analysis occurs in which each value $YP_K$ is compared with the average or mean value of all of the $YP_K$ elements. If the following equation is met, the capsule is accepted:

[te,ovs/YP/ $-YP_K$]≦LVL4 (Eq. 4). where, LVL4 is a fourth reference value. If the separate YP values differ significantly from the mean value of YP there is an indication of a curve or other shape to the edge which differs from a straight line. If equation 4 is not met the capsule is rejected.

While a particular embodiment has been shown and described it would be apparent to one skilled in the art that variations and modifications may be made without departing from the scope of my invention. It is the purpose of the attached claims to cover all such variations and modifications.

What is claimed is:

1. Apparatus for automatically checking a product which has at least one element which, when viewed two-dimensionally, is normally a straight line, including;

a raster-scanned photo-electric converter for viewing said product;

synchronization-signal stripping means coupled to said converter and responsive to a composite signal therefrom to produce, separately, horizontal and vertical drive signals, and a video signal free of such drive signals;

signal-shaping means coupled to said stripping means and responsive to said video signal therefrom to produce a series of binary signals representative of said video signal;

signal processing means coupled to said signal-shaping means and responsive to shaped signals therefrom to detect binary transitions therein corresponding to lines viewed by said photo-electric converter;

first counting means coupled to said signal processing means and to said stripping means and responsive to signals from said processing means and to horizontal drive signals from said stripping means to evaluate the "Y" lengths and "Y" coordinates of said lines viewed by said photo-electric converter;

an "X"-pulse generator;

"X"-counting means coupled to said stripping means and to said "X" pulse generator for determining the "X" coordinates of said at least one element viewed by said photo-electric converter;

memory means having stored therein predetermined reference length information and being coupled to said first counting means and to said "X" counting means for storing the "Y" length, "Y"-coordinate and "X"-coordinate information therefrom, and, automatic calculating means coupled to said memory means for calculating from said stored "Y"-length, "Y" coordinate, "X"-coordinate and predetermined reference length information whether the longest viewed line is at least of said predetermined reference length; and, control means coupled to said automatic calculating means and responsive to a calculation that the longest viewed line is of at least said predetermined reference length to accept said product and responsive to a calculation that said longest viewed line is not of said predetermined reference length to reject said product.

2. Apparatus according to claim 1 in which said photo-electric converter is a television camera.

3. Apparatus according to claim 1 in which said calculating means is a micro-computer.

4. Apparatus according to claim 1 in which said raster-scanned photo-electric converter has a field of view and which includes, in addition, conveyor means for conveying said product through said field of view of said photo-electric converter.

5. Apparatus according to claim 4 which includes in addition strobe means for illuminating said product during viewing thereof by said photo-electric converter.

6. The method of controlling the quality of a product having an element which, when viewed two-dimensionally, is normally a straight line, which method includes the steps of:

viewing the product in orthogonal "X" and "Y" directions with a photo-electric converter having a raster-scan including a vertical scanning signal representing a "Y" direction and a number of horizontal scanning lines lying in an "X" direction, each horizontal scanning line having a time period and each being displaced in a "Y" direction from the other by a predetermined distance as a result of said vertical scanning signal in said raster-scan, said photo electric converter producing a video signal;

shaping the video signal from said photo-electric converter to produce a series of binary signals representative of said video signal;

storing said binary signals;

counting the number of horizontal scanning line periods which are contained in each line viewed by said converter to give a length-count representative of the length of that line in a "Y" direction;

electronically comparing the lengths in the "Y" direction of each line so viewed to determine the line of maximum length in the "Y" direction;

comparing the length of said line of maximum length in the "Y" direction with a stored reference length; and generating a product-reject signal if the length of said line of maximum length in a "Y" direction is shorter than said stored reference length.

* * * * *